United States Patent
Wingfield

(10) Patent No.: US 10,905,124 B2
(45) Date of Patent: *Feb. 2, 2021

(54) ANTIMICROBIAL SOLUTION AND METHODS OF MAKING AND USING THE SAME

(71) Applicant: Ag21 Health Sciences, LLC, Richmond, VA (US)

(72) Inventor: William Wingfield, Richmond, VA (US)

(73) Assignee: Ag21 Health Sciences, LLC, Richmond, VA (US)

( * ) Notice: Subject to any disclaimer, the term of this patent is extended or adjusted under 35 U.S.C. 154(b) by 225 days.

This patent is subject to a terminal disclaimer.

(21) Appl. No.: 14/813,341

(22) Filed: Jul. 30, 2015

(65) Prior Publication Data

US 2015/0373984 A1 Dec. 31, 2015
US 2018/0116225 A9 May 3, 2018

Related U.S. Application Data

(63) Continuation of application No. 14/319,292, filed on Jun. 30, 2014, now Pat. No. 9,132,296, which is a continuation of application No. 12/152,712, filed on May 16, 2008, now abandoned.

(60) Provisional application No. 60/930,535, filed on May 17, 2007.

(51) Int. Cl.

| | | |
|---|---|---|
| *A01N 55/02* | (2006.01) | |
| *A61K 8/365* | (2006.01) | |
| *A61Q 5/02* | (2006.01) | |
| *A61Q 5/12* | (2006.01) | |
| *A61Q 15/00* | (2006.01) | |
| *A61Q 17/00* | (2006.01) | |
| *A61K 8/02* | (2006.01) | |
| *A61K 8/19* | (2006.01) | |
| *A01N 59/16* | (2006.01) | |
| *A61Q 19/10* | (2006.01) | |

(52) U.S. Cl.
CPC ............ *A01N 55/02* (2013.01); *A01N 59/16* (2013.01); *A61K 8/0208* (2013.01); *A61K 8/19* (2013.01); *A61K 8/365* (2013.01); *A61Q 5/02* (2013.01); *A61Q 5/12* (2013.01); *A61Q 15/00* (2013.01); *A61Q 17/005* (2013.01); *A61Q 19/10* (2013.01)

(58) Field of Classification Search
None
See application file for complete search history.

(56) References Cited

U.S. PATENT DOCUMENTS

| | | |
|---|---|---|
| 1,482,906 A | 2/1924 | Allen |
| 4,136,145 A | 1/1979 | Fuchs et al. |
| 4,592,920 A | 6/1986 | Murtfeldt |
| 4,677,143 A | 6/1987 | Laurin et al. |
| 4,847,049 A | 7/1989 | Yamamoto |
| 4,847,078 A | 7/1989 | Sheppard et al. |
| 4,849,223 A | 7/1989 | Pratt et al. |
| 4,933,178 A | 6/1990 | Capelli |
| 5,019,096 A | 5/1991 | Fox, Jr. |
| 5,676,977 A | 10/1997 | Antelman |
| 5,848,995 A | 12/1998 | Walder |
| 5,895,782 A | 4/1999 | Overton et al. |
| 6,258,385 B1 | 7/2001 | Antelman |
| 6,583,176 B2 | 6/2003 | Arata |
| 6,716,895 B1 | 4/2004 | Terry |
| 6,756,059 B2 | 6/2004 | Roszell et al. |
| 6,838,095 B2 | 1/2005 | Newman et al. |
| 6,881,421 B1 | 4/2005 | Da Silveira et al. |
| 6,916,468 B2 | 7/2005 | Lasota |
| 6,949,598 B2 | 9/2005 | Terry |
| 7,135,195 B2 | 11/2006 | Holladay et al. |
| 7,179,849 B2 | 2/2007 | Terry |
| 7,262,179 B2 | 8/2007 | Court et al. |
| 7,311,927 B2 | 12/2007 | Miner et al. |
| 7,378,156 B2 | 5/2008 | Terry |
| 7,557,094 B2 | 7/2009 | Wadstein |
| 7,700,131 B2 | 4/2010 | Taylor et al. |
| 8,034,454 B2 | 10/2011 | Terry |
| 9,393,261 B2 | 7/2016 | Sternoff et al. |

(Continued)

FOREIGN PATENT DOCUMENTS

| | | |
|---|---|---|
| JP | 7-165510 A | 6/1995 |
| JP | 8-268821 | 10/1996 |

(Continued)

OTHER PUBLICATIONS

Chung, Y.-C. et al., Acta Pharmacologica Sinica, "Relationship between antibacterial activity of chitosan and surface characteristics of cell wall", 2004, vol. 25, No. 7, pp. 932-936 (Year: 2004).*

(Continued)

*Primary Examiner* — Bahar Craigo
(74) *Attorney, Agent, or Firm* — Myers Bigel, P.A.

(57) ABSTRACT

A chitosan solution is formed from chitin, which is a homopolymer of beta (1-4)-linked N-acetyl-D-glucosamine. Rinsed, dried and ground chitin undergoes a process of deacetylation to convert some N-acetyl glucosamine to glucosamine, a primary component of chitosan. The chitosan solution is prepared by mixing 5chitosan with a alpha-hydroxy acid such as glycolic acid. An aqueous chelated silver solution is prepared by mixing silver oxide with a carboxylic acid such as citric acid. The chitosan solution can then be mixed with the silver solution resulting in a cationic complex. The cationic complex of the present invention may then be electrostatically bonded with generally negatively charged surfaces. In use, citrate promotes uptake of the silver by microbes. The antimicrobial complex can be applied via several methods of application, including an impregnated wipe, a foam, a gel, a spray, a lotion and an ointment.

20 Claims, 3 Drawing Sheets

(56) References Cited

U.S. PATENT DOCUMENTS

| | | |
|---|---|---|
| 2002/0192311 A1 | 12/2002 | Sakai |
| 2004/0009210 A1 | 1/2004 | Koenig et al. |
| 2004/0022858 A1 | 2/2004 | Antelman |
| 2004/0043048 A1 | 3/2004 | Nomura et al. |
| 2005/0042173 A1 | 2/2005 | Besse et al. |
| 2005/0158405 A1* | 7/2005 | Boukas .............. A61K 31/045 424/725 |
| 2005/0250194 A1 | 11/2005 | Taylor et al. |
| 2006/0074029 A1 | 4/2006 | Leece |
| 2006/0105057 A1 | 5/2006 | Antelman |
| 2007/0264204 A1 | 11/2007 | Noor et al. |
| 2008/0045491 A1 | 2/2008 | Fitchmun |
| 2008/0311206 A1 | 12/2008 | Student et al. |
| 2009/0018190 A1 | 1/2009 | Ebert et al. |
| 2009/0035342 A1 | 2/2009 | Karandikar et al. |
| 2010/0120915 A1 | 5/2010 | Beierle |
| 2010/0316749 A1 | 12/2010 | Fossel |
| 2013/0022643 A1* | 1/2013 | Sternoff .............. A61K 31/722 424/400 |
| 2013/0224308 A1 | 8/2013 | De Windt et al. |
| 2014/0314820 A1 | 10/2014 | Wingfield |
| 2015/0079141 A1 | 3/2015 | Wingfield |
| 2015/0351406 A1 | 12/2015 | Wingfield et al. |
| 2015/0373984 A1 | 12/2015 | Wingfield |

FOREIGN PATENT DOCUMENTS

| | | |
|---|---|---|
| JP | 2010202561 | 9/2010 |
| JP | 2012177901 | 1/2012 |
| RU | 2271814 | 3/2006 |
| WO | 2004/028461 | 4/2004 |
| WO | WO2006015317 A2 | 2/2006 |
| WO | 2006/074359 | 7/2006 |
| WO | 2006/094387 | 9/2006 |
| WO | WO 2014/092747 | 6/2014 |

OTHER PUBLICATIONS

Janssen, D. E. et al., Organic Syntheses, "4-Iodoveratrole", 1963, coll. vol. 4, p. 547 (and published 1956, vol. 36, p. 46).

Hu, Z. et al., Mater. Res. Soc. Symp. Proc. vol., "Suspension of Silver Oxide Nanoparticles in Chitosan Solution and its Antibacterial Activity in Cotton Fabrics", 2006, vol. 920, 6 total pages.

Muzzarelli, R. A. A. et el., Int. J. Biol. Macromol., "Solubility and structure of N-carboxymethylchitosan", vol. 16, No. 4, pp. 177-180, 1994.

International Preliminary Report on Patentability and Written Opinion corresponding to International Application No. PCT/US2016/040294, dated Jan. 30, 2018, 14 pages.

Huang et al, "Preparation and characterization of metal-chitosan nanocomposites," Colloids and Surfaces B: Biointerfaces, 39, pp. 31-37 (2004).

Unites States Non-Final Office Action corresponding to U.S. Appl. No. 15/098,772, dated Mar. 28, 2018, 27 pages.

Cheung et al., Chitosan: An Update on Potential Biomedical and Pharmaceutical Applications, Mar. Drugs 2015, 13, 5156-5186; DOI:10.3390/md13085156 (Year: 2015).

Supplementary European Search Report, EP 15859742, dated Jul. 2, 2018, 8 pages.

International Search Report and Written Opinion, PCT/US2013/000273, dated May 22, 2014 8 pages.

International Search Report and Written Opinion, PCT/US2015/060507, dated Mar. 22, 2016, 7 pages.

"Chelate" https://science.jrank.org/pages/1375/Chelate.html (2 pages) (retrieved online on Jun. 21, 2019).

Desbriers et al. "Surfactant-Chitosan Interactions and Application to Emulsion Stabilization" Cellulose Chemistry and Technology, 44(9):395-406 (2010).

Goycoolea et al. "Chitin and chitosan" Developments in Food Science, 41:265-308 (2000) (Abstract only).

Lu et al. "Preparation of Strong Cationic Chitosan-graft-Polyacrylamide Flocculants and Their Flocculating Properties" Industrial & Engineering Chemistry Research, 50(12):7141-7149 (2011) (Abstract only).

Nicu et al. "Chitosan as Cationic Polyelectrolyte in Wet-End Papermaking Systems" Cellulose Chemistry and Technology, 45(1-2):105-111 (2011).

Pranantyo et al. "Chitosan-Based Peptidopolysaccharides as Cationic Antimicrobial Agents and Antibacterial Coatings" Biomacromolecules, 19(6):2156-2165 (2018) (Abstract only).

* cited by examiner

| 10 | Prepare Chitosan |
|----|----|
|  |  |
| 11 | Provide raw material |
| 12 | Remove non-chitin components |
| 13 | Dry and grind to desired size |
| 14 | Deacetylation |
| 15 | Rinse |

FIG. 1

| 20 | Prepare Chitosan Solution |
|----|----|
|  |  |
| 21 | Provide deionized water |
| 22 | Provide Chitosan powder |
| 23 | Provide alpha-hydroxy acid |
| 24 | Mix |

FIG. 2

| 30 | Prepare Aqueous Silver Solution |
|----|-------------------------------------|
|    |                                     |
| 31 | Provide silver salts                |
| 32 | Provide alkaline solution           |
| 33 | Create silver oxide                 |
| 34 | Provide carboxylic acid             |
| 36 | Provide deionized water             |
| 37 | Provide light impervious container  |

FIG. 3

| 40 | Prepare Antimicrobial Complex |
|----|-----------------------------------|
|    |                                   |
| 41 | Provide Chitosan Solution         |
| 42 | Provide deionized water           |
| 43 | Provide Aqueous Chelated Silver Solution |
| 44 | Mix until homogenous              |

FIG. 4

| 50 | Apply complex |
|----|-------------------|
|    |                   |
| 51 | Determine surface to disinfect |
| 52 | Determine appropriate application |
| 53 | Use application to apply complex to surface to instantaneously and residually kill bacteria |

FIG. 5

ANTIMICROBIAL SOLUTION AND METHODS OF MAKING AND USING THE SAME

This application is a continuation of and claims priority on and the benefit of Ser. No. 14/319,292, filed Jun. 30, 2014 and entitled, "ANTIMICROBIAL SOLUTION AND METHODS OF MAKING AND USING THE SAME", which is a continuation of Ser. No. 12/152,712, filed May 16, 2008 which is a nonprovisional conversion of provisional application 60/930,535 filed May 17, 2007, all sharing the same title, the entire contents of which are hereby incorporated herein by reference.

BACKGROUND OF THE INVENTION

Field of the Invention

The present invention relates to an antimicrobial topical solution 5 comprising complexes of chitosan-silver, and in particular to solutions comprising complexed chitosan-silver bio-films, and to the methods of making the same.

Description of the Related Art

Topical antimicrobial solutions, or simply antimicrobial solutions, are widely used in today's society. Some uses are prophylactic, such as when a hand sanitizer is used prior to consuming a meal. Other times, users use a topical antimicrobial solution after encountering germs and microbes and prior to resuming to normal activities, such as immediately after using the bathroom and before returning to work. The latter scenario hopefully is routine for restaurant personnel. Healthcare acquired infections cause approximately to 103,000 deaths annually. This number of deaths is more than the combined total resulting from AIDS, breast cancer and automobile accidents. The economic burden is over \$5.2 billion. It is the $4^{th}$ 20 leading cause of death. Inadequate hand hygiene also contributes to food-related illnesses, such as salmonella and *E coli* infection. According to the The Center for Disease Control and Prevention (hereafter, the "CDC"), as many as 76 million Americans contract a food-borne illness each year. Of these, about 5,000 die as a result of their illness. Others experience the annoying symptoms of nausea, vomiting and diarrhea. The CDC lists hand hygiene as the number one preventive measure against the spread of healthcare acquired infections. The CDC came out with hand hygiene guidelines to better address the problem in October, 2002. The CDC made a strong recommendation for the use of hand sanitizers even when hands are not 5 visibly soiled. Since the CDC guidelines were published, hand sanitizer sales in the United States have enjoyed double-digit growth, according to marketing information company A.C. Nielsen. Through December 2006, more than \$70 million in all brands of hand sanitizers have been sold in U.S. supermarkets and drugstores, up 14.4 percent from the year before. The largest sales growth in recent years came in 2005, when more than \$67.3 million in sanitizers were sold, a whopping 53.5 percent increase from 2004, according to A.C. Nielsen figures. The total annual U.S. infection prevention industry is \$9.4 billion. Antimicrobial solutions can be applied in many forms. For example, many soaps contain antimicrobial agents that are used in combination with other soap ingredients. Hand sanitizers often come in forms of sprays, gels, lotions, ointments and other forms that a user rubs on his or her hands to kill present bacteria. The use of alcohol or quaternary ammonium chloride compounds is common in these types of solutions. Yet, the affects of these chemicals diminish greatly shortly after application. These current hand sanitizers are either flammable or, as in some cases, are showing less than effective results against more stubborn bacterial strains. Antimicrobial agents can also be applied with a wipe, such as a moist disposable towel. Some disposable towels utilize bleach or other chemicals that can have harsh and unintended consequences on a user's skin. Silver is naturally present in our environment, including the air we breathe, the water we drink and the foods we consume. However, silver does not occur naturally in the tissues of humans and animals. Silver is of extremely low toxicity to animals and humans. It is however, extremely toxic to simpler forms of life such as bacteria.

The antibacterial properties of silver have been known or suspected for thousands of years. The ancient Greeks used silver pots and other utensils. Hippocrates, the father of modern medicine, wrote that silver had beneficial healing and anti-disease properties. The Phoenicians stored water, wine and vinegar in silver bottles to prevent spoiling. In the early 1900s, it was not uncommon for people to place silver dollars in milk bottles to prolong the freshness of the milk. The malleability and non-toxicity of silver make it a useful material used in dental alloys for fittings and fillings. The widespread use of silver went out of fashion as an antimicrobial solution with the development of modern antibiotics. Many antibiotic drugs can be used to kill pathogens, but overuse has led to increased bacteria resistance to many of the antibiotics. Hence, there has recently been renewed interest in silver as a broad spectrum antimicrobial. Silver, when applied topically, continually demonstrates efficacy against microorganisms which have otherwise exhibited resistance characteristics. There are products on the market to treat or kill bacteria. These products are in a variety of forms, including liquid, foam, gel, lotion and ointment. Some of these products are described in the following patents:

U.S. Pat. No. (Hereafter, "USPN") 4,847,049 to Yamamoto is titled Method of Forming Chelated Collagen Having Bactericidal Properties. This patent provides a method for protecting renatured collagen against bacterial and fungal attack. The method includes contacting the collagen with a silver ion containing solution at a pH range of 4.0 to 9.0 and exposing the silver-chelated collagen to ultraviolet radiation.

U.S. Pat. No. 6,756,059 to Rozell et al. is titled Topical Composition, Topical Composition Precursor, and Methods for Manufacturing and Using. This patent discloses a topical composition precursor prepared by melt processing a hydrophobic polymer composition that includes repeating pyrrolidone/alkylene groups wherein the alkylene groups contain at least 10 carbon atoms, and a hydrophobic polymer composition including repeating carboxylic groups and/or hydroxyl groups.

U.S. Pat. No. 6,716,895 to Terry is titled Polymer Compositions Containing Colloids of Silver Salts. This patent teaches how to provide varying release kinetics for the active ions in the compositions due to different water solubilities of the ions, allowing antimicrobial release tailored to a given application. The polymer compositions are stated to contain colloids comprised of salts of one or more oligodynamic metals such as silver.

U.S. Pat. No. 7,135,195 to Holladay et al. is titled Treatment of Humans with Colloidal Silver Composition. The composition includes water and silver particles, wherein the silver particles comprise an interior of elemental silver and an exterior of ionic silver oxide. The silver particles are described to be present in the water at a level of about 5-40 parts per million (Hereafter, "ppm").

U.S. Pat. No. 6,881,424 to Kemp is titled Highly Acidic Metalated Organic Acid. This 20 patent teaches how to mix a monovalent or polyvalent cation and an organic acid in the presence of a strong oxyacid. The resulting composition is described to be less corrosive to a ferrous metal than a solution of a mineral acid having the same acidic pH value, and is more biocidal than a mixture of the organic acid and a metal salt of the organic acid which mixture has the same acid normality value.

U.S. Pat. No. 5,895,782 to Overton et al. is titled Acid Replacement Solution for Cleaning of Non Ferrous Metals. This patent is taught to be used to clean non ferrous alloys such as copper, brass and high strength aluminum alloys. The solution is described to be prepared by mixing $Ca(OH)_2$ and KOH with equivalent sulfuric acid in water, and then passing the solution through a 10 micron filter.

U.S. Pat. No. 6,383,095 to Newman et al. is titled Ionic Silver Complex. The invention is described to be made by combining ingredients water, a source of free silver ions, and a substantially non-toxic, substantially thiol-free, substantially water soluble complexing agent. This patent claims the use of an alkali metal and/or alkaline earth metal used as a counter-ion.

U.S. Pat. No. 6,583,176 to Arata is titled Aqueous Disinfectant. The aqueous solution is formulated by electrolytically generating silver ions in water in combination with a citric 15 acid.

None of these patents describe the use of silver complexed with chitosan to form an antibacterial complex bio-film which allows for the silver complex to remain in contact with the surface of the skin and effectively kill bacteria for hours. It is an object of the present invention to provide an antimicrobial solution having high immediate or short term effectiveness. It is another object of the present invention to provide an antimicrobial solution having high residual effectiveness.

It is a further object of the present invention to provide an antimicrobial solution that readily bonds to a user's skin such that it remains in place.

It is a still further object of the present invention to provide an antimicrobial solution that is stable, portable and easily dispensable.

It is a still further object yet of the present invention to provide 5 an antimicrobial solution that is gentle and that does not provide harsh consequences for a user's skin.

Thus there exists a need for an antimicrobial solution that solves these and other problems.

SUMMARY OF THE INVENTION

The present invention relates to an antimicrobial topical solution comprising complexes of chitosan-silver, and in particular to solutions comprising complexed chitosan-silver bio-films, and to the methods of making the same. The present invention is non-colloidal.

In one embodiment, the chitosan solution is formed by first providing chitin, which is a homopolymer of beta (1-4)-linked N-acetyl-D-glucosamine. Rinsed, dried and ground chitin can then undergo a process of deacetylation to convert some N-acetyl glucosamine to glucosamine, a primary component of chitosan. The chitosan solution can then be prepared by mixing chitosan with an alpha-hydroxy acid such as glycolic acid and allowing it to thicken. An aqueous silver solution can be prepared by mixing silver oxide with a carboxylic acid such as citric acid to form silver chelate. These carboxylic groups readily form the acid/base (citrate) complex. The chitosan solution can then be mixed with the silver solution. Since the chitosan solution is cationic, and the silver solution may be generally neutral, the resulting silver-chitosan complex will be cationic. The cationic solution of the present invention will bond nicely with the generally negatively charged human skin. In use, citrate promotes uptake of the silver by bacteria. The antimicrobial solution can be processed for application via several 5 methods, such as through a foam dispenser, a pump, a saturated wipe, spray, lotion and/or ointment. According to one advantage of the present invention, an antimicrobial solution having high immediate or short term effectiveness is provided. This is accomplished as bacteria are attracted to the citrate in the solution. The citrate promotes uptake of the silver ion in the bacteria, resulting in the killing of the bacteria. In fact, the present invention comprising the chitosan-silver complex has been evaluated by independent laboratory testing to be effective against salmonella, *e-coli*, MRSA (staph), *Pseudomonas aeroginosa, Serratia marcescens* and *Klebsiella pnuemoniae*.

According to another advantage of the present invention, an antimicrobial solution having high residual effectiveness is provided. This is accomplished as the antimicrobial solution is relatively stable and does not evaporate. Related and according to a further advantage of the present invention, an antimicrobial solution that readily bonds to a user's skin such that it remains in place is provided. This is accomplished because in the chitosan-silver complex of the present invention, the silver is bonded to the chitosan as a complex and thus forms a molecule that is positively charged or cationic. The skin of the human body typically exhibits a negative charge and accordingly is anionic. The natural electrostatic attraction of the chitosan-silver complex to the surface of the skin allows complex to bond with the skin. In fact, laboratory results have shown a 75 ppm chitosan-silver complex to have a residual efficacy of two and one half hours under laboratory conditions. This is achieved without the use of synthetic polymers and without the utilization of alcohol, benzalkonium chloride or triclosan. The chelated silver is the active ingredient that quickly dispatches the bacteria upon contact.

According to a still further advantage yet of the present invention, an antimicrobial solution that is stable, portable and easily dispensable is provided. The present invention is non-colloidal. According to a still further advantage yet of the present invention, an antimicrobial solution that is gentle and that does not provide harsh consequences for a user's skin is provided. This is accomplished as the present invention is not known to promote irritation of the skin.

Other advantages, benefits, and features of the present invention will become apparent to those skilled in the art upon reading the detailed description of the invention and studying the drawings.

BRIEF DESCRIPTION OF THE DRAWINGS

FIG. 1 is a flow chart showing a preferred embodiment of the process of making chitosan from chitin.

FIG. 2 is a flow chart showing a preferred embodiment of the process of making a chitosan solution.

FIG. 3 is a flow chart showing a preferred embodiment of the process of making an aqueous silver solution.

FIG. 4 is a flow chart showing a preferred embodiment of the process of preparing the antimicrobial complex of the present invention.

FIG. 5 is a flow chart showing the process of applying the complex of the present invention.

DETAILED DESCRIPTION OF THE PREFERRED EMBODIMENTS

While the invention will be described in connection with one or more preferred embodiments, it will be understood that it is not intended to limit the invention to those embodiments. On the contrary, it is intended to cover all alternatives, modifications and equivalents as may be included within the spirit and scope of the invention as defined by the appended claims.

Looking now to FIG. 1, a process 10 of forming chitosan is provided. Raw material is provided in step 11. The raw material is chitin. Chitin is a homopolymer of beta (1-4)-linked N-acetyl-D-glucosamine. Chitin is an abundant naturally occurring and renewable resource bio-polymer. Chitin is found in exoskeletons of invertebrates. In a preferred embodiment, chitin is derived from the family of decapod crustaceans such as shrimp and prawns. Chitin obtained in this manner generally has a molecular weight of approximately between 500 and 900 kDalton. Process 10 is necessary to the present invention as chitin is insoluble.

The chitin is processed by removing non-chitin components in step 12. This step is accomplished in one embodiment through the use of hydrochloric acid (HCL). The HCL removes or strips any residual meat tissue that is attached to the shell. It is appreciated that other acids or methods of stripping the residual meat tissue can be incorporated without departing from the broad aspects of the present invention. After the residual meat tissue is stripped, a solution of Sodium Hydroxide (NaOH) is used to rinse and neutralize the exoskeletons. In the preferred embodiment, a NaOH solution of approximately 20% is used.

Step 13 involves drying the chitin and processing the chitin to have a desired size. Preferably, the chitin is ground so that it has an average size of approximately 24 mesh (0.0278 inches average particle dimension).

Step 14 is deacetylation. This step 14 involves in a preferred embodiment mixing 1 part chitin with 4 parts 50% NaOH, which is a base to which had been added 1 part of pure water. The resulting mixture comprises 5 parts total, of which the solution has 40% NaOH per 1 part chitin. The mixture is heated to approximately 70 degrees Celsius for about 72 hours to undergo the process of deacetylation. The process of deacetylation converts some of the N-acetyl glucosamine to glucosamine. The result of deacetylation is the aggregation and precipitation of chitosan molecules.

Step 15 is to rinse the chitosan to remove remaining NaOH and any other impurities. In the preferred embodiment, the step 15 of rinsing the chitosan comprises a triple rinse. Yet, it is appreciated that other numbers of rinses could alternatively be used without departing from the broad aspects of the present invention. It is preferable that the chitosan is then allowed to dry. Turning now to FIG. 2, the step 20 of making a 2% chitosan solution is provided.

The following preferred embodiment yields approximately 1 liter, or 1000 mls. The first step 21 in this process 20 is to provide deionized water. 182 mls. of deionized water is measured and placed under moderate to high agitation. 20 grams of chitosan (rinsed and dried) is then provided in step 22, and measured. The chitosan powder is dispersed into and mixed with the deionized water under moderate to high agitation. Next, in step 23, an alpha-hydroxy acid such as glycolic acid is provided. In the preferred embodiment, glycolic acid is used for its lack of strong odor, and is of approximately 70% purity. It is understood that other alpha-hydroxy acids may be used without departing from the broad aspects of the present invention. Approximately 45 mls. of glycolic acid is then mixed with the deionized water and chitosan under moderate agitation in step 24. After the mixture begins to thicken, it can be placed under a paddle mixer. Approximately 35 additional mls. of the glycolic acid can be added, and the mixture can be mixed slowly for approximately an additional 45 to 60 minutes. After this period of time, the mixture is preferably viscous. The chitosan solution is preferably ready when it achieves the desired viscosity.

Turning now to FIG. 3, a method 30 of preparing an aqueous silver solution is provided. First, in step 31, silver salts can be provided. Then, an alkaline solution can be provided in step 32, and mixed with the silver salts. The result, in step 33, is the formation of silver oxide. Once silver oxide is created, a citric acid can be provided in step 34, and deionized water can be provided in step 36.

After the ingredients are provided, they can be combined in a mixing vessel of either high density plastic or glass. The following steps are utilized to yield a 1 liter, or 1000 ml batch of constituted 1000 ppm chelated silver solution. Solution A is prepared by mixing approximately 2.65 grams of citric acid with 797.35 grams of distilled water, and mixing for approximately 5-10 minutes. Slurry 1 is prepared by adding approximately 1.10 grams silver oxide to approximately 198.9 grams distilled water and dispersing for approximately 5-10 minutes. The dispersed silver oxide in water Slurry 1 can be slowly added to Solution 1 and mixed at a high speed for approximately 30-45 minutes. The resulting silver chelate will be colorless and odorless. Remove from agitation, filter through a qualitative analysis filter paper, such as VWR, 415 and set aside in a light impervious container. It is appreciated that the solubility of the silver oxide is strongly affected by the ligands present in the solution. Citric acid is chosen because of its innate ability to form a complex with the silver and because of its recognition as a universal constituent of animals and plants as well as the human body. While citric acid is a preferred component, it is understood that other carboxylic acids may be used without departing from the broad aspects of the present invention. These carboxylic groups readily form the acid-metal (citrate) complex. The silver is first dispersed in the distilled water to form a thin slurry so that there is a larger exposure of the surface area of the silver oxide molecule to the citric acid. The $Ag_2O$ molecule is only slightly soluble in an aqueous solution, hence the necessary addition of citric acid to the mixture. The silver ion forms a coordination compound as a result of this Lewis acid-base reaction. The silver ion here is the acid (acceptor) and the citric acid ligand is the base (donor). Turning now to FIG. 4, the method 40 of preparing the antimicrobial solution of the present invention is shown. In this method 40, the steps are provide chitosan solution in step 41, provide deionized water in step 42, provide aqueous silver solution in step 43 and mix until homogeneous in step 44. In particular the formed solution is a bio-film forming sanitizer that is cationic and bio-adhesive, and contains chelated silver in a concentration sufficient to effect residual antibacterial activity for hours.

The following ratios are used in order to achieve a 1 liter batch, or 1000 mls. batch. First, in steps 41 and 42, approximately 500 mls. of 2% chitosan solution and approximately 400 mls. of deionized water are provided. The chitosan and deionized water are preferably mixed slowly for approximately 3 minutes. Next, in step 43, approximately 100 mls.

of the 1000 ppm silver solution is provided. The silver solution is added to the mixture of chitosan and deionized water in step 44, and the solution is preferably mixed slowly for an additional 3 minutes. The resulting solution is a formulation containing 100 ppm silver and bio-bonding chitosan. It is appreciated that all vessels and agitators in this method 40 are preferably made of high density plastic or glass, and must be free of metallic surfaces.

It is understood that other ratios of chitosan solution to silver solution can be used without departing from the broad aspects of the present invention.

FIG. 5 demonstrates the process 50 for applying the complex. Step 51 comprises determining the surface or substrate to disinfect. Step 52 comprises the step of determining the proper application, or application means is then determined based on the nature of the surface or substrate to disinfect. Step 53 comprises the step of using the application to apply the complex to the intended surface or substrate.

The antimicrobial solution of the present invention can be further processed for a wide variety of dispensing methods. The dispensing methods can include foaming pumping, spraying or wiping with a pre-moistened, impregnated or saturated wipe. Still further, the complex can be incorporated into lotions, gels and/or ointments. In operation, the cationic properties of the solution allow it to bond with a person's or animal's skin, which is negatively charged. It is understood that the general category of animals is intended to include humans.

The effectiveness of the solution is partly derived from the inclusion of the citrate, as bacteria are attracted to and feed on the citrate. Citrate promotes the uptake of the silver ion which indicates that the complex is of the transported species. Citrate is abundantly found in nature, and is a natural constituent of all living cells. Accordingly, most bacteria have a cytoplasmic membrane that mediates or controls the uptake of citrate and accordingly complexes of citrate. Mechanistically the transporters couple the uptake of citrate is coupled with the uptake of one or more protons or potassium ions. Yet, according to the present invention, the citrate is complexed with silver ions, and the bacteria accordingly take up the silver citrate complex. The bacteria rapidly die after taking up the silver, as the silver immediately disables vital proteins and the bacteria's metabolic and reproductive functions and the organisms tend to die within minutes.

The chitosan-silver complex is cationic and bonds readily to negatively charged human or animal skin. The chitosan-silver complex can't cause silver poisoning like colloidal (ionic) silver. This is due to the mechanism of the molecule itself. When absorbed into the skin the complex immediately becomes inert because it binds with the free sodium that occurs naturally in our bodies and on our skin. It then is excreted out through our kidneys.

Three examples follow:

Example 1

A 500 ml amount of 100 ppm hand sanitizer was prepared in the following manner:
Solution A
  0.265 gms. Citric Acid and add to
  299.735 gms. Distilled Water
  Mix 5-10 minutes
Slurry 1
  0.11 gms. Silver Oxide and add to
  99.89 gms. Distilled Water
  Disperse 5-10 minutes Take prepared Solution A and place under moderate agitation for the stipulated time. Slowly add the previously dispersed silver oxide in water Slurry 1 and mix at high speed for 30-45 minutes. The resulting silver chelate will be colorless and odorless. Remove from agitation, filter through a qualitative analysis filter paper, such as VWR 20 415, and set aside in a light impervious container. The silver is now ready to be used as a hand sanitizer. Take 30 mls of the 2% chitosan solution and to it add 70 mls distilled water. Mix for 1 minute and then add to the 400 mls of prepared chelated silver. Mix all for 3 minutes before use. The solution may be made to foam by the addition of a salt free surfactant such as Mackam 2CSF available from McIntyre Group Ltd. The surfactant can be used at ratios from 0.001 to 10% of the formulation. The addition of a botanical such as aloe vera or chamomile can enhance the sensory appeal of the sanitizer. An alternate method of foaming can be accomplished by using a natural foamer like an agave derivative such as is offered by Desert King out of California.

Example 2

The product may be utilized as the solution to impregnate both non woven and natural fiber wipes.

A 500 ppm sanitizer solution was prepared in the following manner:
Solution A
  0.685 gms. Citric Acid and add to
  299.315 gms. Distilled Water
  Mix 5-10 minutes
Slurry 1
  0.275 gms. Silver Oxide and add to
  99.725 gms. Distilled Water
  Disperse 5-10 minutes Take 15 ml of 2% chitosan solution and add to 85 mls distilled water and mix for 1 minute. Add the resulting solution to the prepared chelated silver and mix slowly for 3 minutes. In this instance it is desirable to incorporate a small amount of an anti fungal/anti mold preservative to inhibit the growth of such organisms in the wipe media once saturated. The exact amount of liquid absorbed is dependent upon the nature of the substrate whether woven or non woven and the surface area to be treated. The amount of silver in such wipes can vary from 10 ppm to over 2,000 ppm. The incorporation of chitosan into the mixture is also variable from 0.0012 to 50%. Also a botanical such as chamomile, lavender and or aloe vera may also be included for added appeal.

Example 3

A lotion also utilizes the chitosan-silver complex in rations from 1 to 2,000 ppm. In this regard, a 100 ppm lotion was produced using a myristyl myristate, cetereth 20 base with the addition of several botanicals and emollients. Again other botanicals can also be incorporated into the silver lotion. It is also desirable to incorporate an anti fungal/anti mold preservative into the lotion to inhibit such growth as Euxyl 500 from Schulke & Mayr GmbH or Phenagon PBD from McIntyre Group Ltd.

The chitosan-silver complex may also be incorporated into a dryer sheet, laundry detergent, shampoo and conditioner for humans and animals, body wash, carpet shampoo, first aid spray for burns or cuts, impregnated into bandages for wound treatment, used as hard surface disinfectant, as a topical to treat skin conditions, as a treatment for clothes and fabrics, as a bio barrier for any surface both non porous and porous. It is further appreciated that the present invention can alternatively be used as a deodorant without departing from the broad aspects of the present invention. Thus it is apparent that there has been provided, in accordance with the invention, an antimicrobial solution and methods of making the same that fully satisfies the objects, aims and advantages as set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

I claim:

1. An aqueous non-colloidal cationic composition comprising water and a silver-chitosan complex, the silver-chitosan complex comprising:
    a silver chelate, wherein the silver chelate is a silver carboxylate complex; and
    cationic chitosan, wherein the silver-chitosan complex is cationic,
    wherein the composition is non-colloidal and cationic, and
    wherein the composition comprises silver in an amount of about 1 ppm to 2000 ppm silver.

2. The composition of claim 1, wherein the composition comprises about 1 ppm to 1000 ppm silver.

3. The composition of claim 1, wherein the composition comprises about 1 ppm to 100 ppm silver.

4. The composition of claim 1, wherein said composition is provided in the form of a liquid, a lotion, a gel, a spray, a foam, and/or an ointment.

5. The composition of claim 4, wherein the composition is a liquid and the liquid is a detergent, a shampoo, a conditioner, a hand sanitizer, a body wash, a deodorant, and/or a carpet shampoo.

6. The composition of claim 1, wherein said composition is impregnated in a bandage, a dryer sheet, and/or a wipe.

7. The composition of claim 1, wherein the composition further comprises a foaming agent selected from the group consisting of an agave derivative, and a salt free surfactant.

8. The composition of claim 1, wherein the composition further comprises a botanical selected from the group consisting of aloe vera and chamomile.

9. The composition of claim 1, wherein the silver-chelate is colorless.

10. The composition of claim 1, wherein the silver-chitosan complex is a bio-adhesive.

11. The composition of claim 1, wherein the silver carboxylate complex is a silver citrate complex.

12. The composition of claim 1, wherein the composition is a solution.

13. A method of treating a wound or burn, comprising administering a therapeutically effective amount of the composition of claim 1 to a subject in need thereof.

14. A method of disinfecting a surface, skin and/or a fabric, comprising applying an effective amount of the composition of claim 1 to said surface, skin and/or fabric.

15. The method of claim 14, wherein the composition is applied to said fabric and said fabric is clothing and/or carpet.

16. The method of claim 14, wherein the composition is applied to said surface and said surface is porous.

17. The method of claim 14, wherein the composition is applied to said surface and said surface is non-porous.

18. The method of claim 14, wherein said composition is provided in the form of a liquid, a lotion, a gel, a spray, a foam, and/or an ointment.

19. The method of claim 14, wherein the composition is a liquid and the liquid is a detergent, a shampoo, a conditioner, a hand sanitizer, a body wash, a deodorant, and/or a carpet shampoo.

20. The method of claim 14, wherein said composition is impregnated in a bandage, a dryer sheet that is contacted with the surface, skin and/or fabric.

* * * * *